United States Patent
Vanasse

(10) Patent No.: US 9,149,363 B2
(45) Date of Patent: Oct. 6, 2015

(54) MODULAR PROXIMAL INTERPHALANGEAL JOINT

(75) Inventor: Thomas M. Vanasse, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 355 days.

(21) Appl. No.: 13/597,338

(22) Filed: Aug. 29, 2012

(65) Prior Publication Data

US 2012/0323338 A1    Dec. 20, 2012

Related U.S. Application Data

(63) Continuation of application No. 12/695,425, filed on Jan. 28, 2010, now Pat. No. 8,303,666.

(51) Int. Cl.
  *A61F 2/42*    (2006.01)
  *A61B 17/68*   (2006.01)
  *A61F 2/30*    (2006.01)

(52) U.S. Cl.
  CPC ............ *A61F 2/42* (2013.01); *A61F 2/4241* (2013.01); *A61F 2002/305* (2013.01);
  (Continued)

(58) Field of Classification Search
  CPC ............ A61F 2002/30622; A61F 2002/30754; A61F 2/4225; A61F 2/4606; A61B 17/7291; A61B 17/3421; A61B 17/7266; A61B 17/8061; A61B 17/164; A61B 17/1682; A61B 17/1686; A61B 5/6826
  See application file for complete search history.

(56) References Cited

U.S. PATENT DOCUMENTS

| | | | |
|---|---|---|---|
| 3,466,669 | A | 9/1969 | Flatt |
| 5,133,761 | A | 7/1992 | Krouskop |

(Continued)

FOREIGN PATENT DOCUMENTS

| | | |
|---|---|---|
| EP | 1527758 A1 | 5/2005 |
| EP | 1627615 A2 | 2/2006 |

(Continued)

OTHER PUBLICATIONS

Examination Opinion of the International Searching Authority for Application No. GB1101121.0 dated Apr. 18, 2011.

(Continued)

*Primary Examiner* — David Isabella
*Assistant Examiner* — Ann Schillinger
(74) *Attorney, Agent, or Firm* — Schwegman Lundberg & Woessner, P.A.

(57) ABSTRACT

A method for replacing a proximal interphalangeal joint with a modular implant assembly is provided. During a first surgical procedure, a first stem component of the implant assembly having a first articulation component removably attached thereto is implanted in a proximal phalanx bone. A second stem component of the implant assembly having a second articulation component removably attached thereto is implanted in a middle phalanx bone. During a second surgical procedure performed after the first surgical procedure, the first articulation component is removed from the first stem component and the second articulation component is removed from the second stem component. A third articulation component is attached to the first stem component and a fourth articulation component is attached to the second stem component. The second surgical procedure is performed without removing the first stem component from the first bone and without removing the second stem component from the second bone.

18 Claims, 8 Drawing Sheets

(52) U.S. Cl.
CPC  *A61F 2002/3038* (2013.01); *A61F 2002/3092* (2013.01); *A61F 2002/30301* (2013.01); *A61F 2002/30332* (2013.01); *A61F 2002/30387* (2013.01); *A61F 2002/30401* (2013.01); *A61F 2002/30484* (2013.01); *A61F 2002/30495* (2013.01); *A61F 2002/30507* (2013.01); *A61F 2002/30574* (2013.01); *A61F 2002/30604* (2013.01); *A61F 2002/30626* (2013.01); *A61F 2002/4248* (2013.01)

(56) References Cited

U.S. PATENT DOCUMENTS

| | | |
|---|---|---|
| 5,147,386 A | 9/1992 | Carignan et al. |
| 5,425,777 A | 6/1995 | Sarkisian et al. |
| 6,699,290 B1 | 3/2004 | Wack et al. |
| 7,175,663 B1 | 2/2007 | Stone |
| 7,431,874 B2 | 10/2008 | Muratoglu et al. |
| 7,498,365 B2 | 3/2009 | Muratoglu et al. |
| 7,790,095 B2 | 9/2010 | Muratoglu et al. |
| 7,906,064 B2 | 3/2011 | Muratoglu et al. |
| 2005/0194723 A1 | 9/2005 | Muratoglu et al. |
| 2009/0265001 A1 | 10/2009 | Muratoglu et al. |

FOREIGN PATENT DOCUMENTS

| | | |
|---|---|---|
| FR | 2734150 A1 | 11/1996 |
| WO | WO-03013398 A1 | 2/2003 |

OTHER PUBLICATIONS

Explor Modular Radial Head, Biomet Orthopedics, 2007, pp. 1-3.
International Search Report for Application No. GB11011121.0 dated Apr. 15, 2011.
Non-Final Office Action for U.S. Appl. No. 12/695,425, Mailed Nov. 9, 2011.
SR PIP Implant System, Small Bone Innovations, Inc., 2007, pp. 1-4.
Swanson Finger Joint Implants, Wright Medical Technology, Inc., 1999, pp. 1-2.
Transforming Extremities, Ascension Orthopedics, Inc., 2009, pp. 1-17.

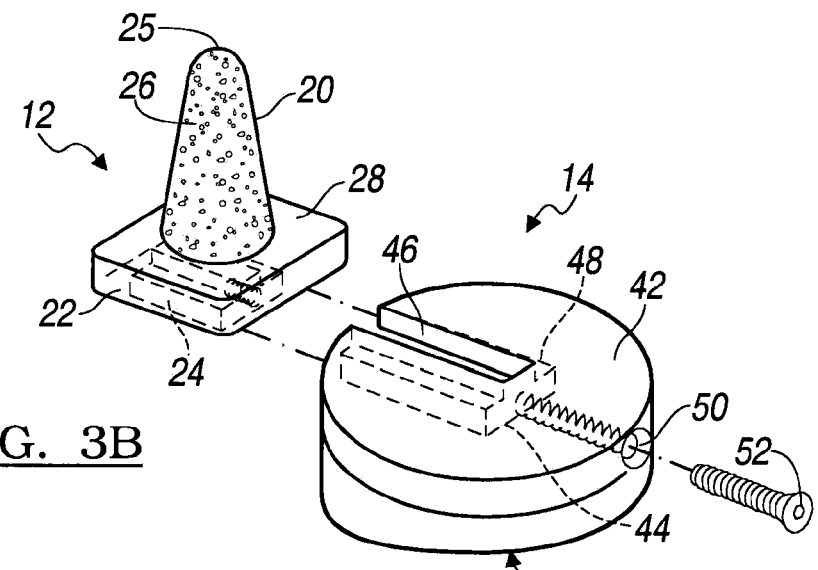
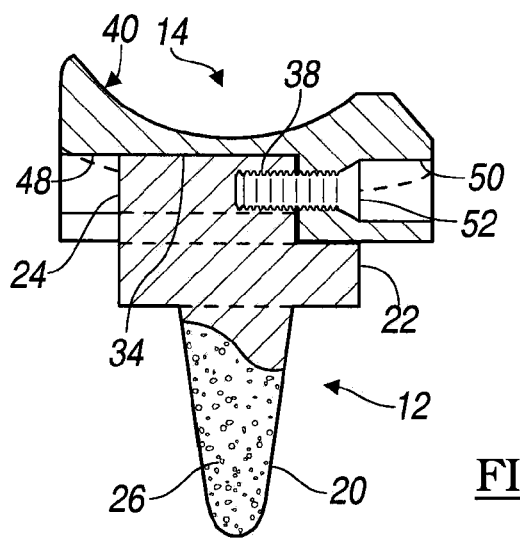
FIG. 3B
FIG. 3C
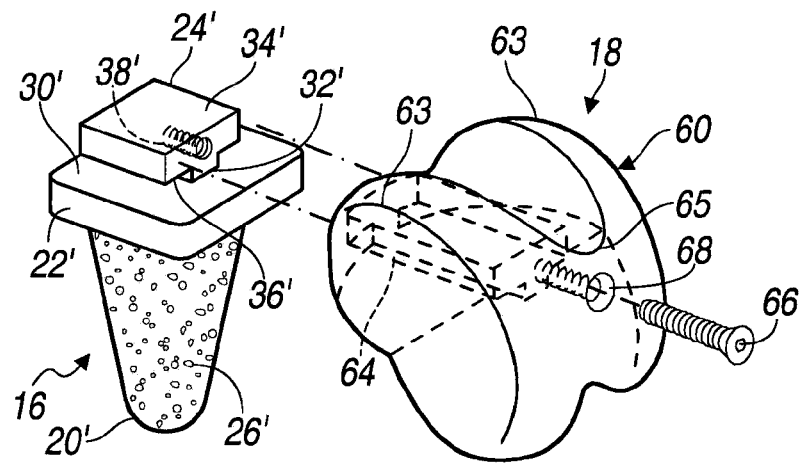
FIG. 4

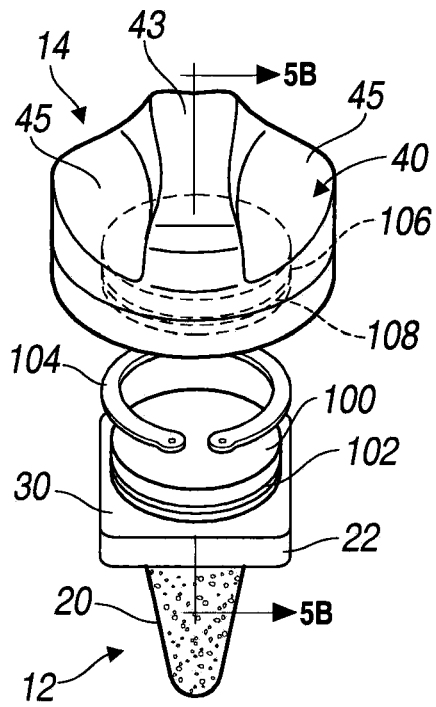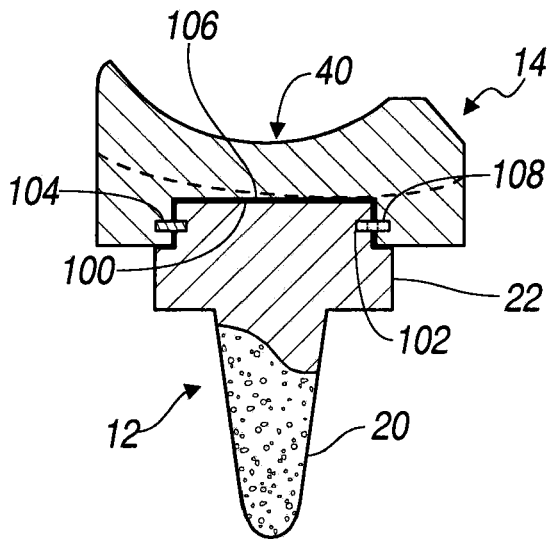
FIG. 5A    FIG. 5B
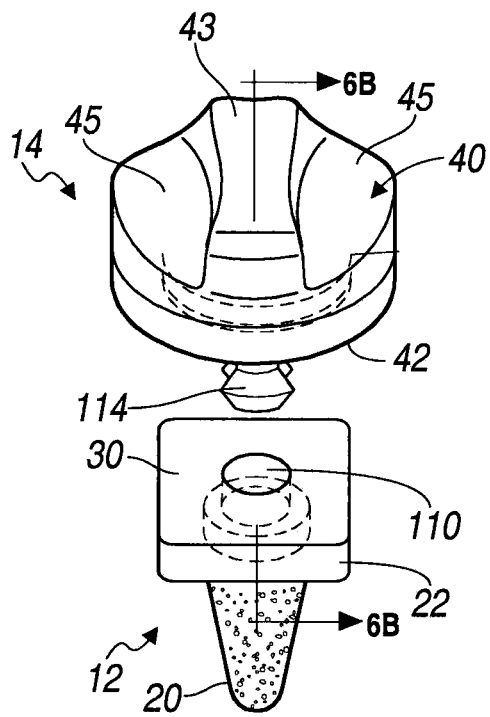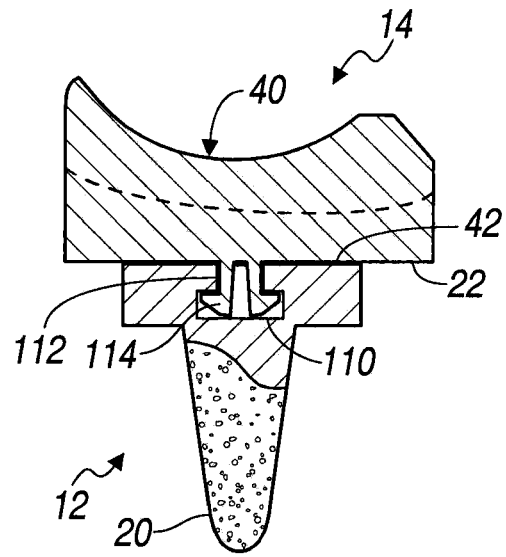
FIG. 6A    FIG. 6B

MODULAR PROXIMAL INTERPHALANGEAL JOINT

CROSS-REFERENCE TO RELATED APPLICATIONS

This application is a continuation of U.S. patent application Ser. No. 12/695,425 filed on Jan. 28, 2010. The entire disclosure of the above application is incorporated herein by reference.

FIELD

The present disclosure relates to anatomical implants, such as a modular proximal interphalangeal joint.

BACKGROUND

This section provides background information related to the present disclosure which is not necessarily prior art.

Disorders of the proximal interphalangeal ("PIP") joint, including trauma and arthritis, can be treated non-surgically with splints, injections, and medications. In severe cases, surgery may be required. Surgical options include fusion and joint replacement. Fusion can relieve pain and restore pinch strength; however, motion in the joint is lost. PIP joint implants can be used to restore joint motion. While current PIP joint implants are suitable for their intended use, they are subject to improvement. For example, there is a need for a PIP joint implant having improved modularity, enhanced sizing options, and enhanced options with respect to degree of joint constraint.

SUMMARY

This section provides a general summary of the disclosure, and is not a comprehensive disclosure of its full scope or all of its features.

The present teachings provide for a method for replacing a proximal interphalangeal joint with a modular implant assembly. The method includes the following: during a first surgical procedure, implanting a first stem component of the implant assembly having a first articulation component removably attached thereto in a proximal phalanx bone and implanting a second stem component of the implant assembly that is substantially the same as the first stem component and has a second articulation component removably attached thereto in a middle phalanx bone, the first articulation component and the second articulation component cooperate to provide the implant assembly with a first degree of articulation constraint; during a second surgical procedure performed after the first surgical procedure, removing the first articulation component from cooperation with the first stem component and removing the second articulation component from cooperation with the second stem component; and further during the second surgical procedure attaching a third articulation component of the implant assembly to the first stem component and attaching a fourth articulation component of the implant assembly to the second stem component, the third articulation component and the fourth articulation component cooperate to provide the implant assembly with a second degree of articulation constraint that is different than the first degree of articulation constraint. The second surgical procedure is performed without removing the first stem component from the first bone and without removing the second stem component from the second bone.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3B is a bottom perspective view of the distal stem and the distal articulation of the implant assembly of FIGS. 1A and 1B;

FIG. 3C is a cross-sectional view taken along line 3C-3C of FIG. 3A;

FIG. 4 is a top perspective view of a proximal stem and a proximal articulation of the implant assembly of FIGS. 1A and 1B;

FIG. 5A is a top exploded perspective view of an additional distal stem and distal articulation in accordance with the present teachings;

FIG. 5B is a cross-sectional view taken along line 5B-5B of FIG. 5A;

FIG. 6A is a top perspective view of another distal stem and distal articulation in accordance with the present teachings;

FIG. 6B is a cross-sectional view taken along line 6B-6B of FIG. 6A;

Corresponding reference numerals indicate corresponding parts throughout the several views of the drawings.

DETAILED DESCRIPTION

Figure 1A:
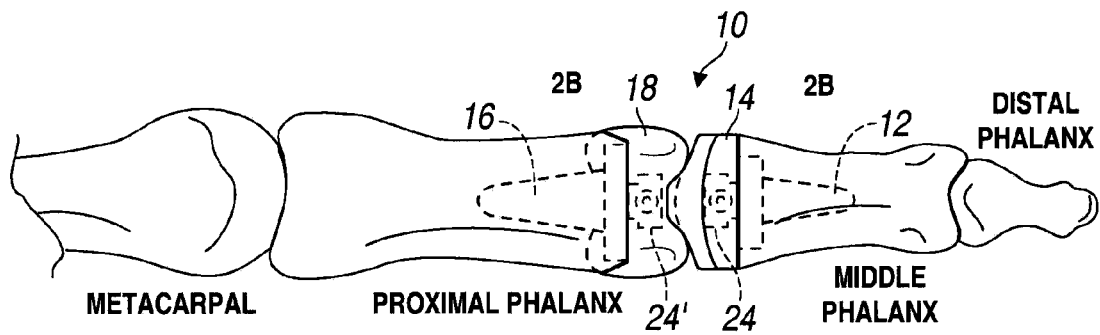
FIG. 1A is a top view of a semi-constrained anatomical implant assembly according to the present teachings implanted in a finger to replace a proximal interphalangeal ("PIP") joint.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below," "lower," "above," "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1B:
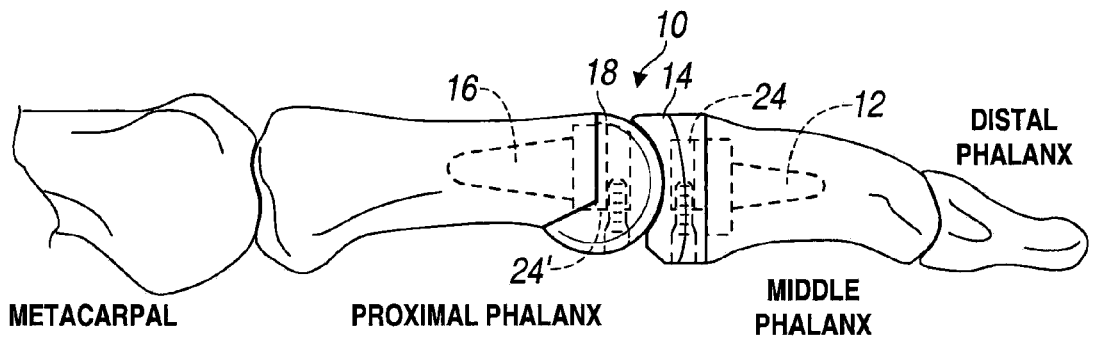
FIG. 1B is a side view of FIG. 1A.

With initial reference to FIG. 1, a proximal interphalangeal ("PIP") joint implant assembly according to the present teachings is illustrated at reference numeral 10. The implant assembly 10 is shown implanted in a human finger to repair the PIP joint, which is located between the proximal phalanx bone and the middle phalanx bone. The implant assembly 10 can provide semi-constrained articulation between the proximal and middle phalanx bones.

Figure 2A:
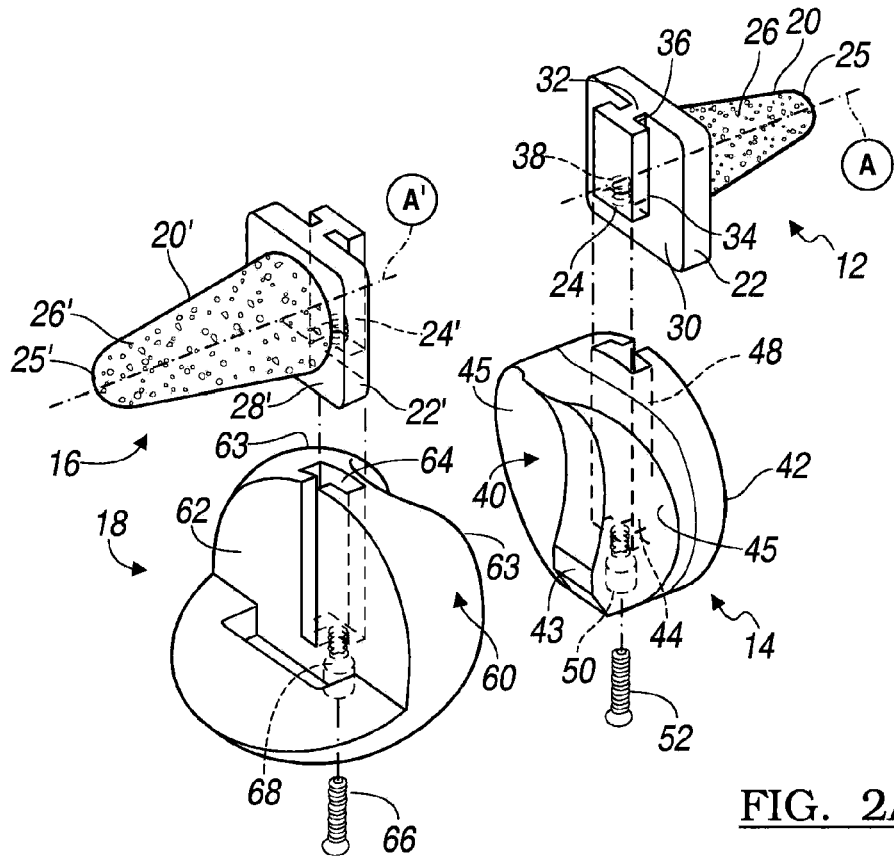
FIG. 2A is an exploded perspective view of the implant assembly of FIGS. 1A and 1B.
Figure 2B:
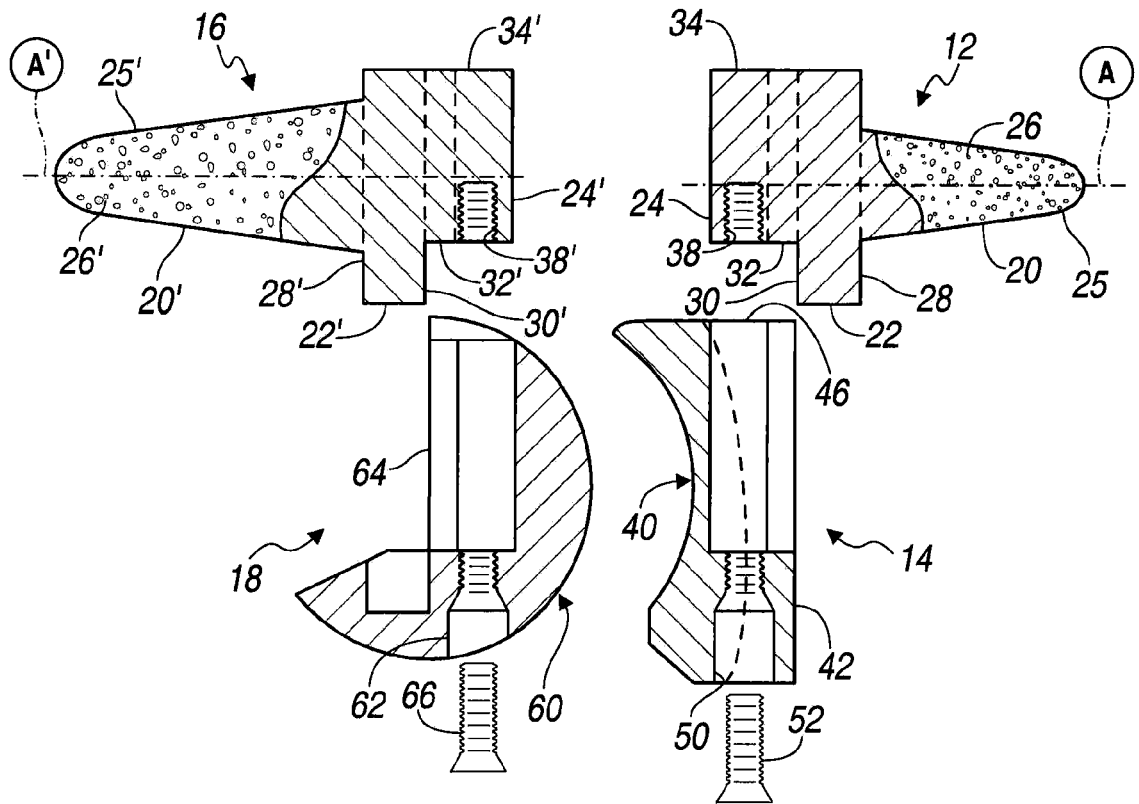
FIG. 2B is a cross-sectional view of the implant assembly of FIG. 1B.
Figure 3A:
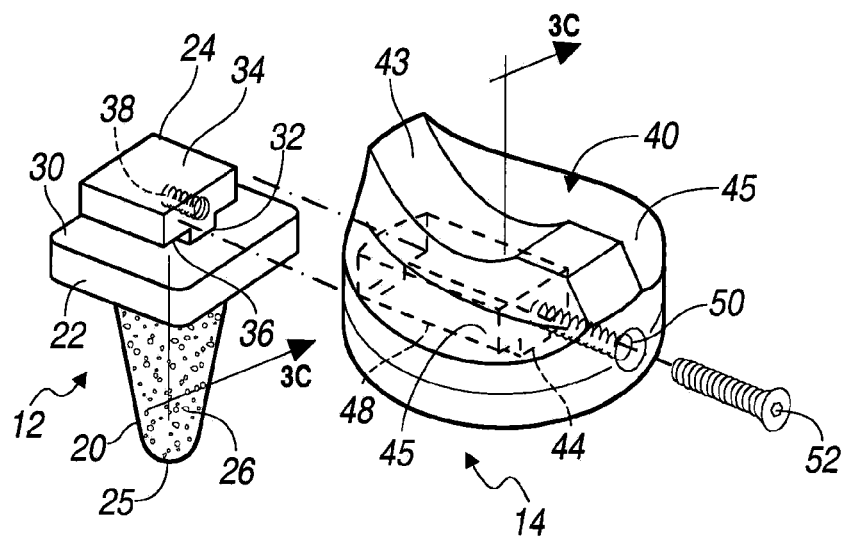
FIG. 3A is a top perspective view of a distal stem and a distal articulation of the implant assembly of FIGS. 1A and 1B.

With additional reference to FIGS. 2-4, the implant assembly 10 generally includes a distal stem 12, a distal semi-constrained articulation 14, a proximal stem 16, and a proximal semi-constrained articulation 18.

The distal stem 12 includes an elongated base portion, or post, 20, a flange 22, and an interlocking detail 24. The elongated base portion 20 is generally conical and tapered from a first end that is proximate to the flange 22 to a second end that is distal to the flange 22 and terminates at a distal tip 25. The elongated base portion 20 can include a porous coating 26 and/or include Regenerex® Porous Titanium Construct to promote bone in-growth, which enhances fixation to the proximal phalanx. Regenerex® is offered by Biomet of Warsaw, Ind. A longitudinal axis A of the post 20 extends through the distal tip 25, through the flange 22, and through the interlocking detail 24.

The flange 22 includes a planar bone engagement surface 28 and a planar articulation support surface 30, which is opposite to the bone engagement surface 28. The planar articulation support surface 30 extends across a plane that is perpendicular to the longitudinal axis A. The elongated base portion 20 extends from the bone engagement surface 28. The interlocking detail 24 is at the planar articulation support surface 30. The bone engagement surface 28 can include the porous coating 26 and/or Regenerex® to enhance fixation between the flange 22 and the proximal phalanx.

The interlocking detail 24 includes a T-shaped rail having a base portion 32 and a connecting flange 34 that each extend across at least a portion of the support surface 30. The connecting flange 34 is mounted to the base portion 32 and is spaced apart from the planar articulation support surface 30 to define a gap 36 there between. The connecting flange 34 defines a bore 38 configured to receive a fastener, as further described herein.

The distal semi-constrained articulation 14 generally includes an articulating surface 40 and a stem engaging surface 42. The stem engaging surface 42 is opposite to the articulating surface 40. As illustrated in FIGS. 1-3, the articulating surface 40 includes a raised center portion 43 that is between, and stands proud of, a pair of side surfaces 45 that generally slope away from the center portion 43 and are shaped to articulate with the proximal articulation 18.

The articulation 14 defines a locking mechanism 44 with an opening 46 that extends from the stem engaging surface 42 to a side of the articulation surface 40. The opening 46 transitions to a locking recess 48 defined within the articulation 14. The locking recess 48 has a generally rectangular shape that is sized to receive the connecting flange 34. A bore 50 extends from an exterior of the articulation 14 to the locking recess 48 and is configured to receive a suitable fastener 52, such as a pin or screw for example. As illustrated in FIG. 3C, with the interlocking detail 24 seated within the locking recess 48, the fastener 52 is inserted through the bore 50 to engage the bore 38 of the connecting flange 34 and secure the distal stem 12 to the articulation 14.

With additional reference to FIG. 4, the proximal stem 16 is substantially similar to the distal stem 12, but has a slightly longer length and/or larger diameter base portion 20'. Therefore, similar features are designated with the same reference numbers; the reference numbers of the proximal stem 16 include the prime (') symbol. With respect to the similar features, the description of the distal stem 12 is sufficient to describe the proximal stem 16 as well.

The semi-constrained proximal articulation 18 generally includes an articulating surface 60 and a stem engaging surface 62 that is opposite to the articulating surface 60. The articulating surface 60 includes a pair of spaced apart lobes 63 that are each generally hemispherical and concave with respect to the stem engaging surface 62 and shaped to articulate with one of the side surfaces 45 of the distal articulation 14. Between the lobes 63 is a recessed surface 65 that is sized and shaped to articulate with the center portion 43 of the distal articulation 14.

The proximal articulation 18 further includes a locking mechanism 64 that is substantially similar to the locking mechanism 44 of the distal articulation 14. To attach the proximal articulation 18 to the proximal stem 16 the interlocking detail 24' is mated with the locking mechanism 64 and a fastener 66 is inserted through a bore 68 of the articulation 18 and secured in the bore 38' of the interlocking detail 24'.

The distal semi-constrained articulation 14 and the proximal semi-constrained articulation 18 can each be made of any suitable material. The articulations 14 and 18 can include similar or different materials in similar or different compositions. For example, each articulation can include a metal, a polymer, or combinations thereof.

Suitable metals include, for example, CoCr, titanium, and combinations thereof. Suitable polymers include one or more of ultra-high molecular weight polyethylene, pyrocarbon, silicone, polyether ether ketone ("PEEK"), carbon fiber reinforced PEEK (such as PEEK-OPTIMA® from Invibio, Ltd. of the United Kingdom), and/or vitamin E stabilized highly crosslinked polyethylene (HXLPE), such as is disclosed in U.S. patent application Ser. No. 10/757,551 by Muratoglu et al., which was filed on Jan. 15, 2004 and issued as U.S. Pat. No. 7,431,874 on Oct. 7, 2008. U.S. Pat. No. 7,431,874 and application Ser. No. 10/757,551 are incorporated by reference herein, as well as are all patent applications and issued patents that rely thereon for priority including the following U.S. patent application Ser. No. 11/104,580 filed on Apr. 13, 2005; Ser. No. 11/104,582 filed on Apr. 13, 2005; Ser. No. 11/564,594 filed on Nov. 29, 2006; Ser. No. 11/948,393 filed on Nov. 30, 2007; and Ser. No. 12/464,235 filed on May 12, 2009. An exemplary vitamin E stabilized HXLPE that may be used includes E-Poly™ offered by Biomet Orthopedics, Inc. of Warsaw, Ind.

Any suitable manner of interconnecting the stems 12 and 16 with the respective articulations 14 and 18 can be used. For example and with reference to FIGS. 5A and 5B, the distal stem 12 can include an interlocking flange 100 extending from a side of the flange 22 opposite to the elongated base portion 20. The flange 100 defines an annular recess 102 in which an annular ring 104 is seated. The annular ring 104 can be made out of any suitable material, such as a metal or a polymer. The articulation 14 defines a cavity 106 that is shaped and sized to receive the flange 100. The cavity 106 defines an annular seat 108. As illustrated in FIG. 5B, to lock the distal articulation 14 to the distal stem 12, the distal articulation 14 is pressed onto the distal stem 12 so that the flange 100 is seated within the annular seat 108 and the annular ring 104 compresses and then snaps into the annular seat 108. This same interlocking arrangement can also be used to attach the proximal semi-constrained articulation 18 to the proximal stem 16.

With additional reference to FIGS. 6A and 6B, the distal stem 12 can define a locking receptacle 110 within the flange 22 and a locking flange 112. The distal semi-constrained articulation 14 can include flexible locking tabs 114 extending from the stem engaging surface 42. The locking tabs 114 are snapped into the locking receptacle 110 to secure the distal semi-constrained articulation 14 to the distal stem 12. This same interlocking arrangement can also be used to attach the proximal semi-constrained articulation 18 to the proximal stem 16.

Figure 7A:
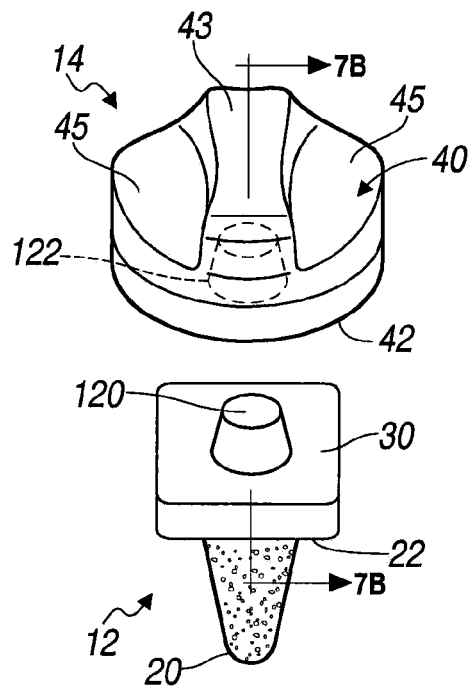
FIG. 7A is a top perspective view of an additional distal stem and distal articulation in accordance with the present teachings.
Figure 7B:
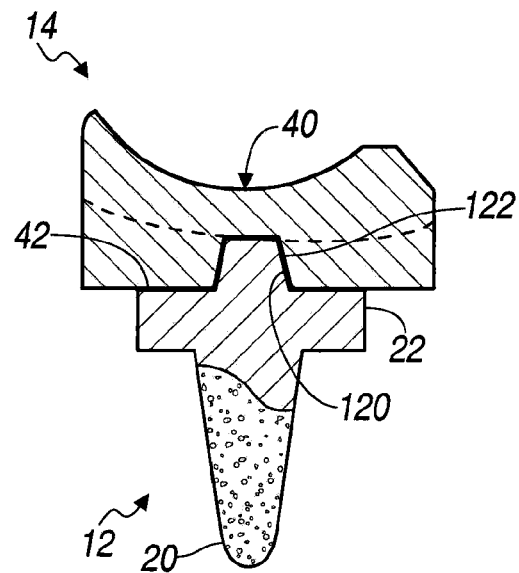
FIG. 7B is a cross-sectional view taken along line 7B-7B of FIG. 7A in accordance with the present teachings.

With additional reference to FIGS. 7A and 7B, the distal stem 12 can include a truncated conical locking protrusion 120 extending from the articulation support surface 30 of the flange 22. The distal semi-constrained articulation 14 can define a conical recess 122 within the stem engaging surface 42 that is sized and shaped to receive the truncated conical locking protrusion 120. The surfaces of the locking protrusion 120 and the conical recess 122 are angled to provide a Morse taper lock there between. Thus, to secure the distal semi-constrained articulation 14 to the distal stem 12, the articulation 14 is seated on the flange 22 so that protrusion 120 mates with the conical recess 122 to form a Morse taper lock. This same interlocking arrangement can also be used to attach the proximal semi-constrained articulation 18 to the proximal stem 16.

Figure 8A:
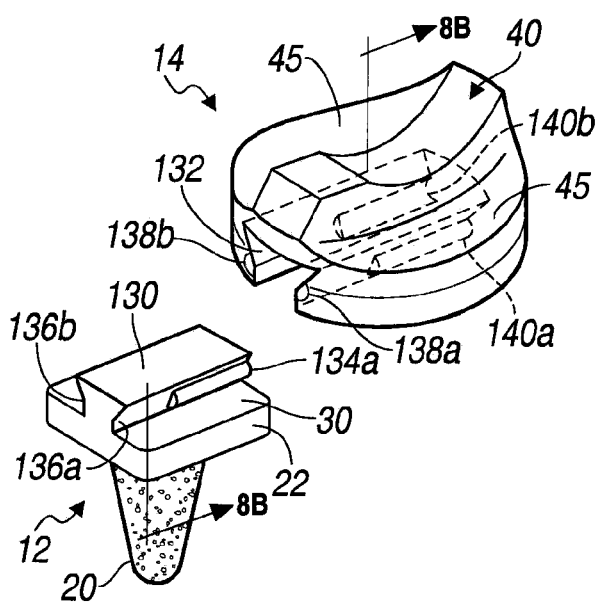
FIG. 8A is a top perspective view of yet another distal stem and distal articulation in accordance with the present teachings.
Figure 8B:
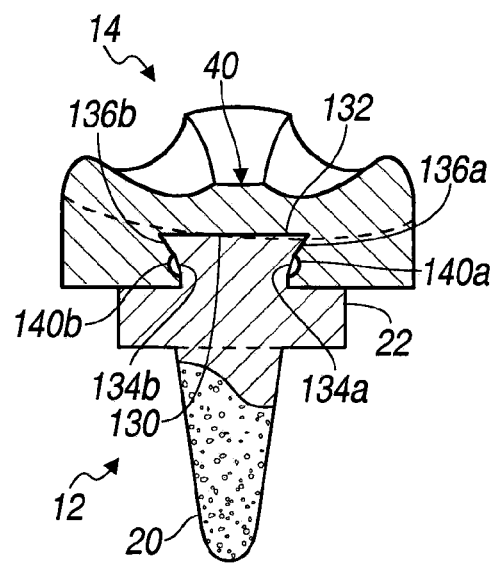
FIG. 8B is a cross-sectional view taken along line 8B-8B of FIG. 8A.

With additional reference to FIGS. 8A and 8B, the distal stem 12 can include a dovetail locking taper 130 extending from the articulation support surface 30 of the flange 22. The taper 130 can include a pair of stem protuberances 134a and 134b that extend respectively from tapered surfaces 136a and 136b of the dovetail locking taper 130. The stem protuberances 134a and 134b each span a distance of approximately one-half a length of the tapered surfaces 136a and 136b respectively. The stem protuberances 134a and 134b are rigid.

The distal semi-constrained articulation 14 can define a dovetail shaped recess 132 sized and shaped to securely receive the dovetail locking taper 130. The recess 132 can include a pair of recess protuberances 138a and 138b. The recess protuberances 138a and 138b include a compressible material such that they can pass by the stem protuberances 134a and 134b as part of a locking mechanism. The recess protuberances 138a and 138b span about one-half a length of the recess 132. The other half of the recess 132 defines concavities 140a and 140b that are sized and shaped to receive the stem protuberances 134a and 134b.

To mount the articulation 14 to the distal stem 12, the articulation 14 is slid over the dovetail locking taper 130 such that the stem protuberances 134a and 134b pass over the compressible recess protuberances 138a and 138b. After the stem protuberances 134a and 134b completely pass over the recess protuberances 138a and 138b, the stem protuberances 134a and 134b can lock into the pair of concavities 140a and 140b respectively. The concavities 140a and 140b are configured in dimension to inversely match the stem protuberances 134a and 134b such that locking occurs. This same interlocking arrangement can also be used to attach the proximal semi-constrained articulation 18 to the proximal stem 16.

The various features described above for coupling the stems 12 and 16 to their respective articulations 14 and 18 include the interlocking details 24 and 24' as part of the stems 12 and 16 and various different interlocking features provided on and defined by the articulations 14 and 18. However, this arrangement can be reversed such that the interlocking details 24 and 24' are at the articulations 14 and 18 and the various other interlocking features of the articulations 14 and 18 are provided on the stems 12 and 16. Furthermore, the interlocking details 24 and 24' are generally described as male members protruding from the respective flanges 22 and 22' and the various interlocking features of the articulations 14 and 18 are generally described as female members recessed within and defined by the articulations 14 and 18. However, this arrangement can be reversed such that the interlocking details 24 and 24' are formed as female members recessed within and defined by the flanges 22 and 22' and the various interlocking features of the articulations 14 and 18 are male members extending from the stem engaging surfaces 42 and 62 and configured to mate with the female interlocking details 24 and 24'.

Figure 9:
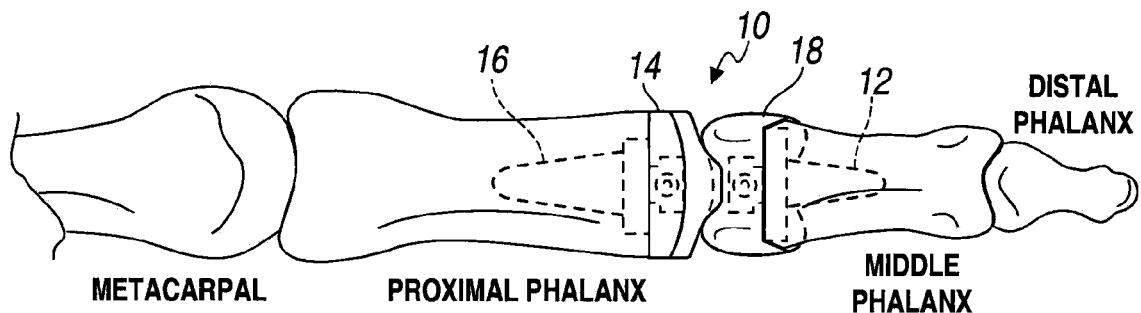
FIG. 9 is a top view of another embodiment of a semi-constrained anatomical implant assembly according to the present teachings implanted in a finger to replace a PIP joint.

With additional reference to FIG. 9, the implant assembly 10 can be reversed such that the distal semi-constrained articulation 14 is mounted to the proximal stem 16 and the proximal semi-constrained articulation 18 is mounted to the distal stem 12.

Figure 10A:
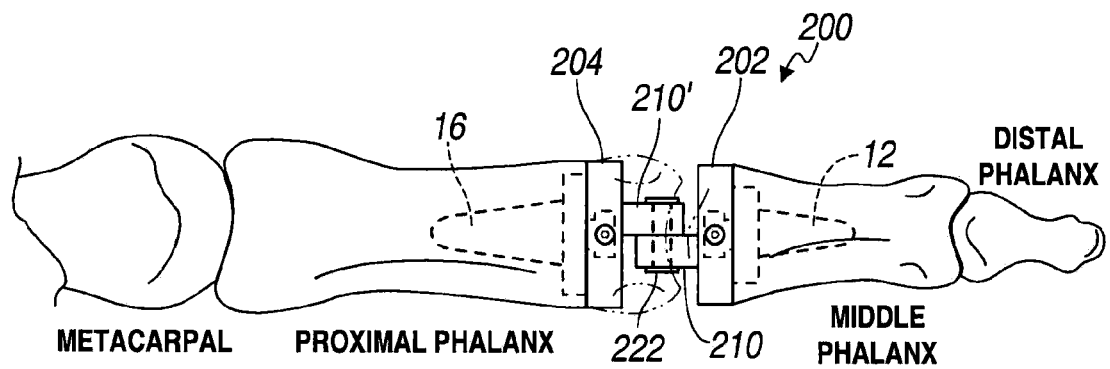
FIG. 10A is a top view of a constrained anatomical implant assembly according to the present teachings implanted in a finger to replace a PIP joint.
Figure 10B:
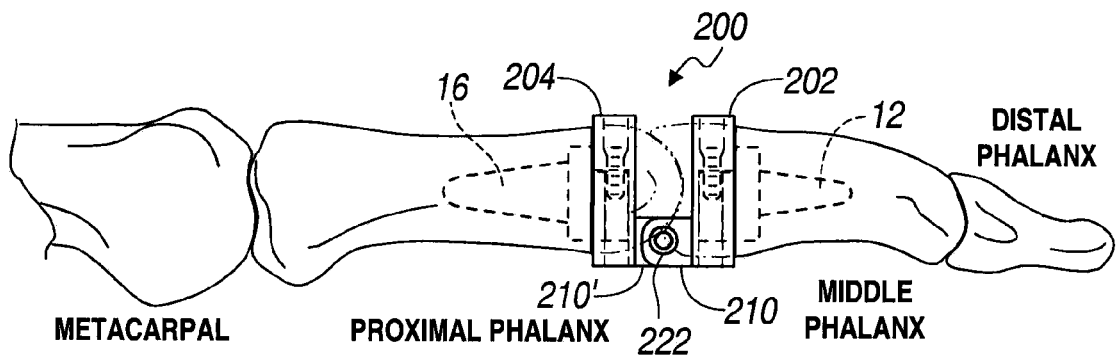
FIG. 10B is a side view of FIG. 10A.

With additional reference to FIGS. 10A and 10B, an additional PIP joint implant assembly according to the present teachings is illustrated at reference numeral 200. The implant assembly 200 can provide constrained articulation between the proximal and middle phalanx bones.

Figure 11A:
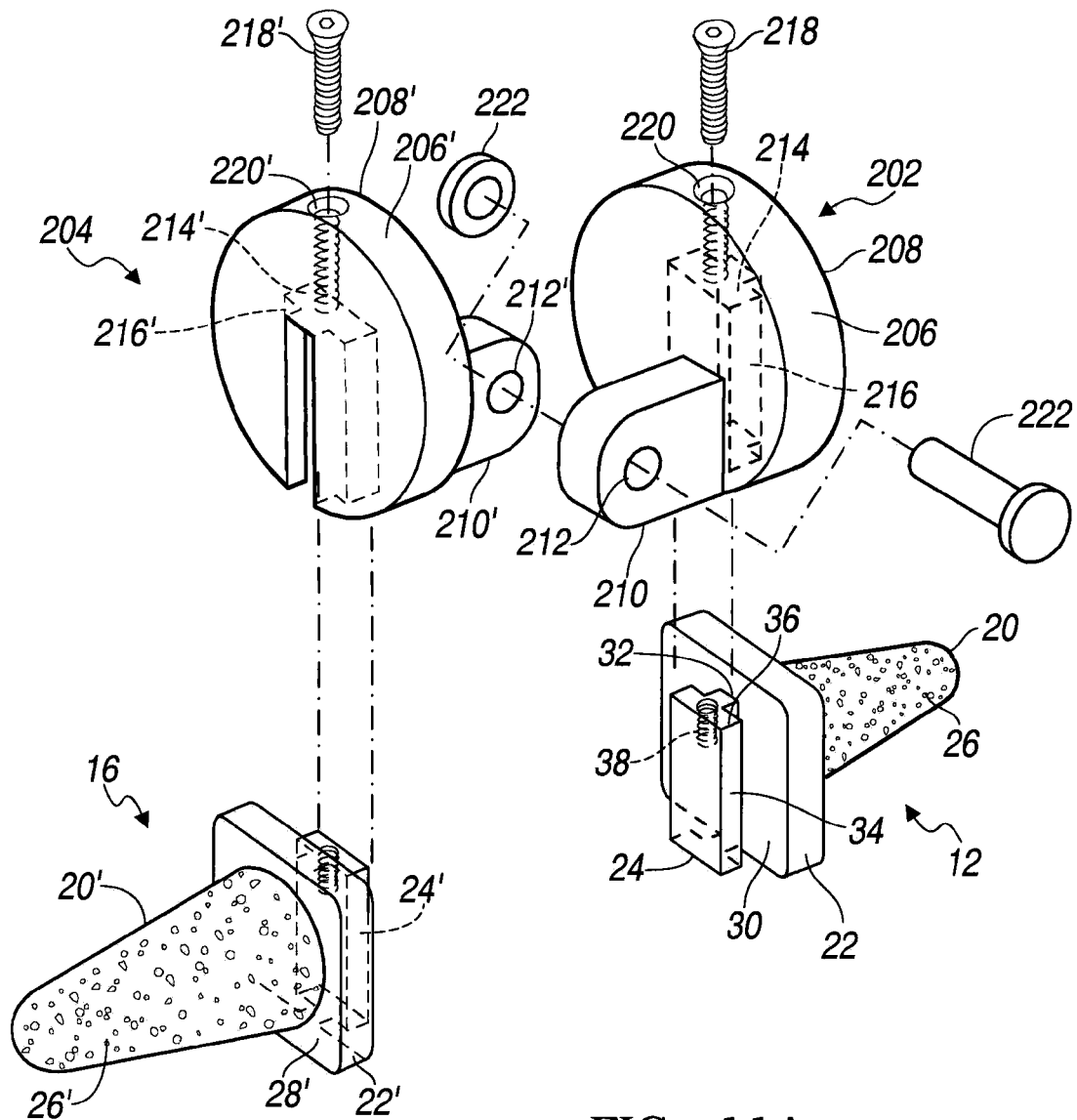
FIG. 11A is an exploded perspective view of the implant assembly of FIGS. 10A and 10B.
Figure 11B:
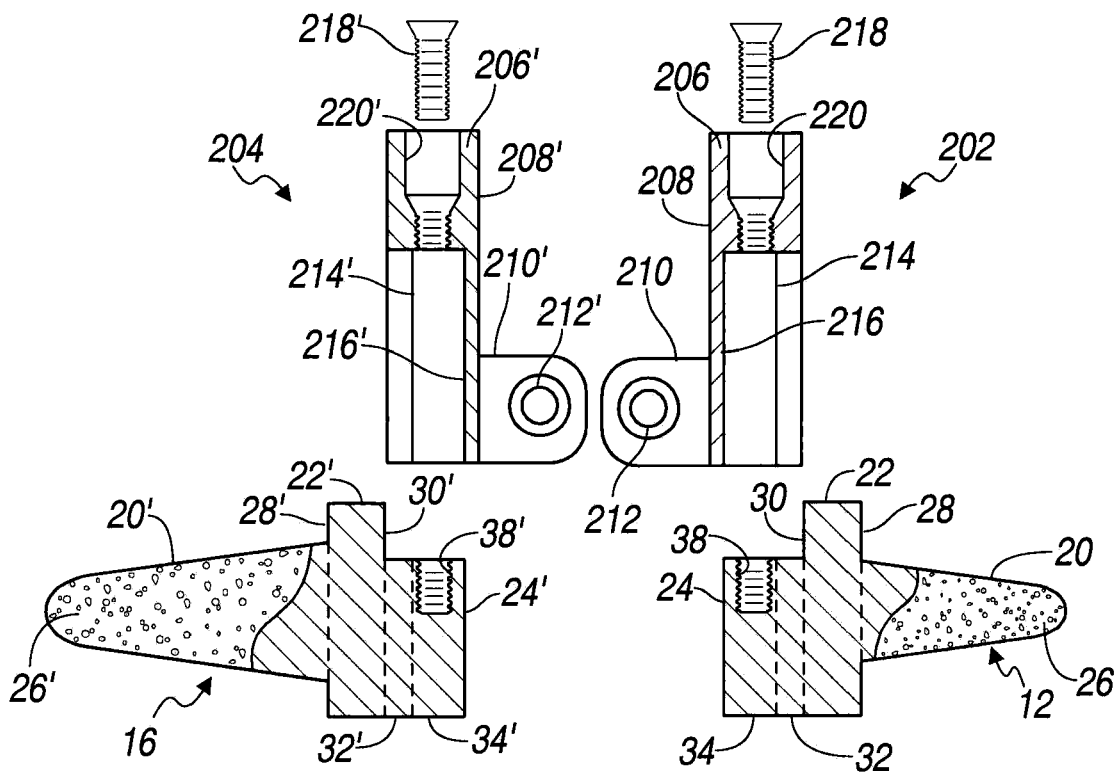
FIG. 11B is a cross-sectional view of FIG. 10B.

With additional reference to FIGS. 11A and 11B, the implant assembly 200 generally includes the same distal stem 12 and the same proximal stem 16 described herein in the context of the implant assembly 10. However, in place of the semi-constrained articulations 14 and 18, a distal constrained articulation 202 and a proximal constrained articulation 204 are provided and mounted to the distal stem 12 and the proximal stem 16 respectively.

The distal constrained articulation 202 includes an articulation base 206 having a stem engaging surface 208 and an articulation flange or hinge 210. The stem engaging surface 208 is generally planar and is on a first side of the articulation base 206. The articulation flange 210 extends from a second side of the articulation base 206 that is opposite to the stem engaging surface 208. The articulation flange 210 is offset from a center of the articulation base 206. The articulation flange 210 defines a through bore 212 having a longitudinal axis that is 90° degrees relative to an axis extending through the center of the articulation base 206.

The articulation base 206 further defines a locking mechanism 214 that is similar to the locking mechanism 44 of the distal articulation 14. The locking mechanism 214 defines a cavity 216 that is shaped and sized to securely receive the interlocking detail 24. With the interlocking detail 24 seated within the cavity 216, a suitable fastener 218, such as a pin or screw, can be inserted through a bore 220 of the articulation base 206 and into engagement with the bore 38 of the interlocking detail 24 to secure the distal articulation 202 to the distal stem 12.

The proximal constrained articulation 204 is substantially similar to the distal constrained articulation 202. Therefore, similar features are designated with the same reference numbers; the reference numbers of the proximal stem 16 and the proximal articulation 204 include the prime (') symbol. With respect to the similar features, the description of the distal articulation 202 is sufficient to describe the proximal articulation 204 as well. As illustrated in FIG. 10, a difference between the distal articulation 202 and the proximal articulation 204 is that the flange 210 of the distal articulation 202 is offset from the flange 210' of the proximal articulation 204 so that the axes of the through bores 212 and 212' align and permit the insertion of a suitable connection device 222, such as a pin, through the bores 212 and 212' to connect the distal articulation 202 to the proximal articulation 204 and allow the articulations 202 and 204 to pivot in a hinge-like manner about the connection device 222.

In place of the locking mechanisms 214 and 214', the distal and proximal articulations 202 and 204, along with the corresponding stems 12 and 16, can include any suitable coupling features, such as those described herein and illustrated in FIGS. 5-8.

The articulations 202 and 204, as well as the connection device 222, can include any suitable biocompatible materials, such as the metal and polymeric materials set forth above in the description of the articulations 14 and 18. The articulations 202 and 204 and the connection device 222 can include the same composition or different compositions. For example, either of the articulations 202 and 204, as well as the connection device 222, can be a metal, a polymer, or combinations thereof.

Figure 12:
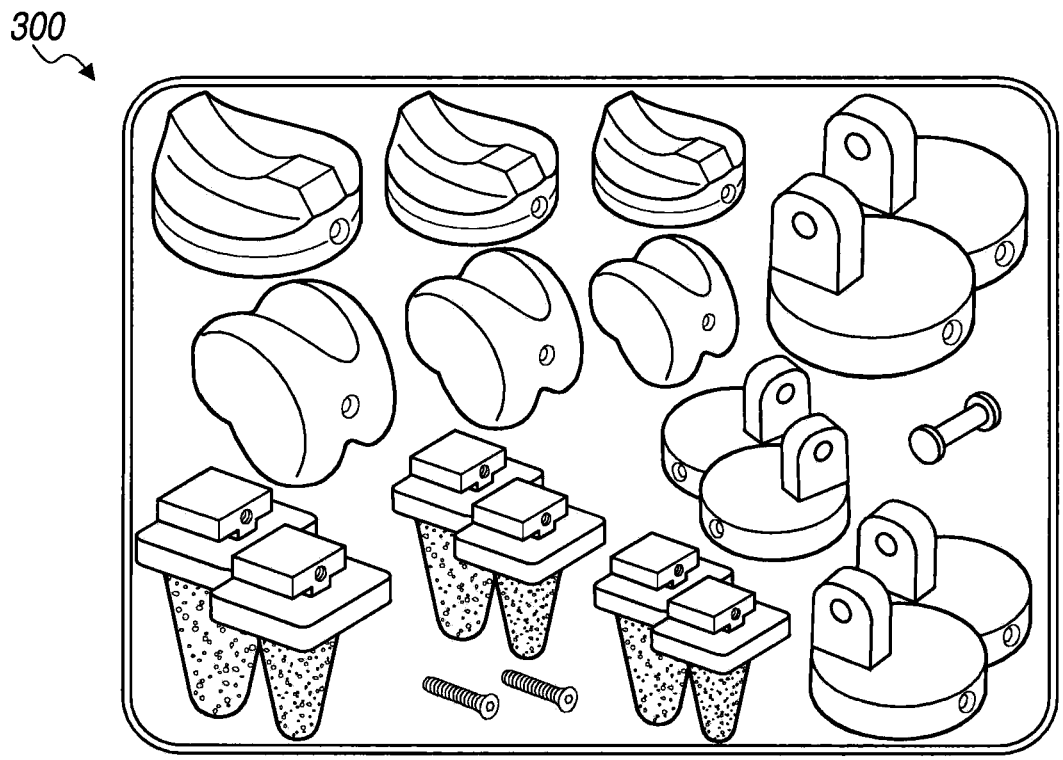
FIG. 12 is an anatomical implant assembly kit according to the present teachings.

With additional reference to FIG. 12, the distal stems 12, the proximal stems 16, the distal semi-constrained articulations 14, the proximal semi-constrained articulations 18, the distal constrained articulations 202, and the proximal constrained articulations 204 can each be provided in various different sizes and configurations, and grouped together in a kit 300. The various features of the distal stems 12 and the proximal stems 16 can vary in size and shape in any suitable manner. For example, the elongated base portions 20 and 20' can vary in length and diameter, the flanges 22 and 22' can vary in surface area and thickness, and the interlocking details 24 and 24' can have varying dimensions. The distal articulations 14 and 202 and the proximal articulations 18 and 204 can also vary in size and shape in any suitable manner to accommodate the stems 12 and 14 that the articulations 14, 18, 202, 204 are connected to and to accommodate various PIP joints of different sizes. The kit 300 can also include the fastener 52 and the connection device 222.

Thus, the present teachings provide for stems 12 and 16 to which either semi-constrained articulations 14 and 18 or constrained articulations 202 and 204 can be mounted to. This allows for conversion between a semi-constrained PIP implant and a constrained PIP implant, such as during a revision procedure or trialing, without having to replace the stems 12 and 16, which are secured within bone in any suitable manner, such as by using bone cement or a press-fit. The implant assemblies 10 and 200 can also be provided with different sized articulations 14, 18, 202, and 204 without having to replace the stems 12 and 16 after they are implanted in bone. Further, the connection device 222 can be replaced without having to replace portions of the remainder of the implant assembly 200.

The present teachings are not limited to application in a PIP implant. The present teachings also apply to a variety of other types of joint replacement implants to provide modular implants having stems that can interchangeably connect to a variety of articulations having different sizes and that provide for varying degrees of constraint. For example, the present teachings also apply to metacarpophalangeal (MCP) joint implants, distal interphalangeal joint (DIP) implants, carpometacarpal (CMC) joints, and other small joints, such as finger or toe joints. The present teachings apply to both total joint replacement and hemi joint replacement as well.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for replacing a proximal interphalangeal joint with a modular implant assembly comprising:
   during a first surgical procedure, implanting a first stem component of the implant assembly having a first articulation component removably attached thereto in a proximal phalanx bone and implanting a second stem component of the implant assembly that is the same as the first stem component and has a second articulation component removably attached thereto in a middle phalanx bone, wherein the first articulation component and the second articulation component cooperate to provide the implant assembly with a first degree of articulation constraint;
   during a second surgical procedure performed after the first surgical procedure, removing the first articulation component from cooperation with the first stem component and removing the second articulation component from cooperation with the second stem component; and
   further during the second surgical procedure attaching a third articulation component of the implant assembly to the first stem component and attaching a fourth articulation component of the implant assembly to the second stem component, wherein the third articulation component and the fourth articulation component cooperate to provide the implant assembly with a second degree of articulation constraint that is different than the first degree of articulation constraint;
   wherein the second surgical procedure is performed without removing the first stem component from the first bone and without removing the second stem component from the second bone.

2. The method of claim 1, wherein the first articulation component includes a convex articulation surface and the second articulation component includes a sloped articulation surface operable to articulate with the convex articulation surface;
   wherein the third articulation component includes a first articulation hinge and the fourth articulation component includes a second articulation hinge operable to articulate with the first articulation hinge and connected to the first articulation hinge with a fastener; and
   wherein the second degree of articulation constraint is greater than the first degree of articulation strength.

3. The method of claim 1, wherein the first articulation component includes a first articulation hinge and the second articulation component includes a second articulation hinge operable to articulate with the first articulation hinge and connected to the first articulation hinge with a fastener; and
   wherein the third articulation component includes a convex articulation surface and the fourth articulation component includes a sloped articulation surface operable to articulate with the convex articulation surface;
   wherein the second degree of articulation constraint is less than the first degree of articulation strength.

4. The method of claim 1, further comprising selecting the first stem component from a plurality of first stem components of different sizes;
   selecting the second stem component from a plurality of second stem components of different sizes;
   selecting the first articulation component from a plurality of first articulation components of different sizes;
   selecting the second articulation component from a plurality of second articulation components of different sizes;
   selecting the third articulation component from a plurality of third articulation components of different sizes; and
   selecting the fourth articulation component from a plurality of fourth articulation components of different sizes.

5. The method of claim 1, further comprising replacing at least one of the first articulation component, the second articulation component, the third articulation component, and the fourth articulation component with a replacement articulation component that is similar to the articulation component being replaced and connecting the replacement articulation component to the stem component that the articulation component being replaced was connected to without removing the stem component from its implantation site.

6. The method of claim 1, wherein attaching the third articulation component to the first stem component and attaching the fourth articulation component to the second stem component further includes attaching the third and fourth components by use of a connection selected from the group comprising a T-shaped rail and flange connection, an annular locking ring connection, flexible locking tab connection, a conical locking protrusion connection, and a dovetail locking taper connection.

7. A method for replacing a proximal interphalangeal joint with a modular implant assembly comprising:
   during a first surgical procedure, implanting a first stem component of the implant assembly having a first articulation component removably attached thereto in a proximal phalanx bone and implanting a second stem component of the implant assembly that has a second articulation component removably attached thereto in a middle phalanx bone;
   during a second surgical procedure performed after the first surgical procedure, removing the first articulation component from cooperation with the first stem component and removing the second articulation component from cooperation with the second stem component; and
   further during the second surgical procedure, attaching a third articulation component of the implant assembly to the first stem component and attaching a fourth articulation component of the implant assembly to the second stem component, wherein the third articulation component and the fourth articulation component are different than the first and second articulation components;
   wherein the second surgical procedure is performed without removing the first stem component from the first bone and without removing the second stem component from the second bone.

8. The method of claim 7, wherein the first articulation component includes a convex articulation surface and the second articulation component includes a sloped articulation surface operable to articulate with the convex articulation surface;
   wherein the third articulation component includes a first articulation hinge and the fourth articulation component includes a second articulation hinge operable to articulate with the first articulation hinge and connected to the first articulation hinge with a fastener; and
   wherein the second degree of articulation constraint is greater than the first degree of articulation strength.

9. The method of claim 7, wherein the first articulation component includes a first articulation hinge and the second articulation component includes a second articulation hinge operable to articulate with the first articulation hinge and connected to the first articulation hinge with a fastener; and wherein the third articulation component includes a convex articulation surface and the fourth articulation component includes a sloped articulation surface operable to articulate with the convex articulation surface;

wherein the second degree of articulation constraint is less than the first degree of articulation strength.

10. The method of claim 7, further comprising selecting the first stem component from a plurality of first stem components of different sizes;

selecting the second stem component from a plurality of second stem components of different sizes;

selecting the first articulation component from a plurality of first articulation components of different sizes;

selecting the second articulation component from a plurality of second articulation components of different sizes;

selecting the third articulation component from a plurality of third articulation components of different sizes; and selecting the fourth articulation component from a plurality of fourth articulation components of different sizes.

11. The method of claim 7, further comprising replacing at least one of the first articulation component, the second articulation component, the third articulation component, and the fourth articulation component with a replacement articulation component that is substantially similar to the articulation component being replaced and connecting the replacement articulation component to the stem component that the articulation component being replaced was connected to without removing the stem component from its implantation site.

12. The method of claim 7, wherein attaching the third articulation component to the first stem component and attaching the fourth articulation component to the second stem component further includes attaching the third and fourth components by use of a connection selected from the group comprising a T-shaped rail and flange connection, an annular locking ring connection, flexible locking tab connection, a conical locking protrusion connection, and a dovetail locking taper connection.

13. A method for replacing a proximal interphalangeal joint with a modular implant assembly comprising:

during a first surgical procedure, implanting a first stem component of the implant assembly having a first articulation component removably attached thereto in a proximal phalanx bone and implanting a second stem component of the implant assembly that has a second articulation component removably attached thereto in a middle phalanx bone;

during a second surgical procedure performed after the first surgical procedure perform the following: separating the first articulation component from the first stem component by, slidably advancing a first locking flange located on one of the first stem component and the first articulation component out from within a locking recess on the other of the first stem component and the first articulation component; removing the second articulation component from cooperation with the second stem component;

attaching a third articulation component of the implant assembly to the first stem component by slidably advancing a third locking flange located on one of the first stem component and the third articulation component into from the locking recess located on the other of the first stem component and the third first articulation component; and attaching a fourth articulation component of the implant assembly to the second stem component; wherein the third articulation component and the fourth articulation component are different than the first and second articulation components.

14. The method of claim 13, wherein the second surgical procedure is performed without removing the first stem component from the first bone and without removing the second stem component from the second bone.

15. The method of claim 13, wherein the first articulation component includes a convex articulation surface and the second articulation component includes a sloped articulation surface operable to articulate with the convex articulation surface;

wherein the third articulation component includes a first articulation hinge and the fourth articulation component includes a second articulation hinge operable to articulate with the first articulation hinge and connected to the first articulation hinge with a fastener; and wherein the second degree of articulation constraint is greater than the first degree of articulation strength.

16. The method of claim 13, wherein the first articulation component includes a first articulation hinge and the second articulation component includes a second articulation hinge operable to articulate with the first articulation hinge and connected to the first articulation hinge with a fastener; and wherein the third articulation component includes a convex articulation surface and the fourth articulation component includes a sloped articulation surface operable to articulate with the convex articulation surface;

wherein the second degree of articulation constraint is less than the first degree of articulation strength.

17. The method of claim 13, further comprising selecting the first stem component from a plurality of first stem components of different sizes;

selecting the second stem component from a plurality of second stem components of different sizes;

selecting the first articulation component from a plurality of first articulation components of different sizes;

selecting the second articulation component from a plurality of second articulation components of different sizes;

selecting the third articulation component from a plurality of third articulation components of different sizes; and selecting the fourth articulation component from a plurality of fourth articulation components of different sizes.

18. The method of claim 13, further comprising replacing at least one of the first articulation component, the second articulation component, the third articulation component, and the fourth articulation component with a replacement articulation component that is substantially similar to the articulation component being replaced and connecting the replacement articulation component to the stem component that the articulation component being replaced was connected to without removing the stem component from its implantation site.

* * * * *

UNITED STATES PATENT AND TRADEMARK OFFICE
CERTIFICATE OF CORRECTION

| | | |
|---|---|---|
| PATENT NO. | : 9,149,363 B2 | Page 1 of 1 |
| APPLICATION NO. | : 13/597338 | |
| DATED | : October 6, 2015 | |
| INVENTOR(S) | : Thomas M. Vanasse | |

It is certified that error appears in the above-identified patent and that said Letters Patent is hereby corrected as shown below:

IN THE CLAIMS

In column 11, line 24, in Claim 11, after "is", delete "substantially", therefor In column 12, line 2, in Claim 13, after "into", delete "from", therefor In column 12, line 3, in Claim 13, after "third", delete "first", therefor In column 12, line 53, in Claim 18, after "is", delete "substantially", therefor Signed and Sealed this
First Day of March, 2016

Michelle K. Lee
*Director of the United States Patent and Trademark Office*